United States Patent [19]
Guempelein et al.

[11] Patent Number: 5,490,008
[45] Date of Patent: Feb. 6, 1996

[54] NON-CONTACTING OPTICAL DATA TRANSMISSION SYSTEM

[75] Inventors: Reinhold Guempelein, Frommetsfelden; Peter Gawlik, Hoechstadt, both of Germany

[73] Assignee: Siemens Aktiengesellschaft, Munich, Germany

[21] Appl. No.: 240,134

[22] Filed: May 10, 1994

[51] Int. Cl.⁶ .................................................. H04B 10/04
[52] U.S. Cl. .................................................. 359/188
[58] Field of Search ............................. 359/159, 180, 359/188, 181; 385/122, 129, 130, 131, 132, 1–5

[56] References Cited

U.S. PATENT DOCUMENTS

| | | | |
|---|---|---|---|
| 4,259,584 | 3/1981 | Krumme | 250/445 T |
| 4,588,895 | 5/1986 | Kürbitz | 359/159 |
| 4,627,106 | 12/1986 | Drake | 359/159 |
| 4,673,241 | 6/1987 | Nishiwaki et al. | 385/2 |
| 5,133,027 | 7/1992 | Funazaki et al. | 385/5 |
| 5,157,393 | 10/1992 | Fox et al. | 340/870.3 |
| 5,367,588 | 11/1994 | Hill et al. | 385/37 |

FOREIGN PATENT DOCUMENTS 1528251  11/1978  United Kingdom .

OTHER PUBLICATIONS

"Optically Addressed Spatial Light Modulators by MBE—Grown nipi MQW Structures," Maserjian et al, Applied Optics, vol. 28, No. 22 (Nov. 15, 1989), pp. 4801–4807.

*Primary Examiner*—Leslie Pascal
*Attorney, Agent, or Firm*—Hill, Steadman & Simpson

[57] ABSTRACT

A non-contacting optical data transmission system, suitable for transmitting data between relatively movable mechanical parts, includes a waveguide, having an high-frequency generator connected at one end and an high-frequency receiver connected at an opposite end, the basic dielectric material of the waveguide being entirely or partially replaced by photosensitive material. An illumination pattern is generated on the waveguide with a light source and a mask, the reflection behavior of the waveguide being modified by this illumination pattern and thereby causing the amplitude of the signal transmitted through the waveguide to be modulated by keying the light source according to the data to be transmitted.

4 Claims, 3 Drawing Sheets

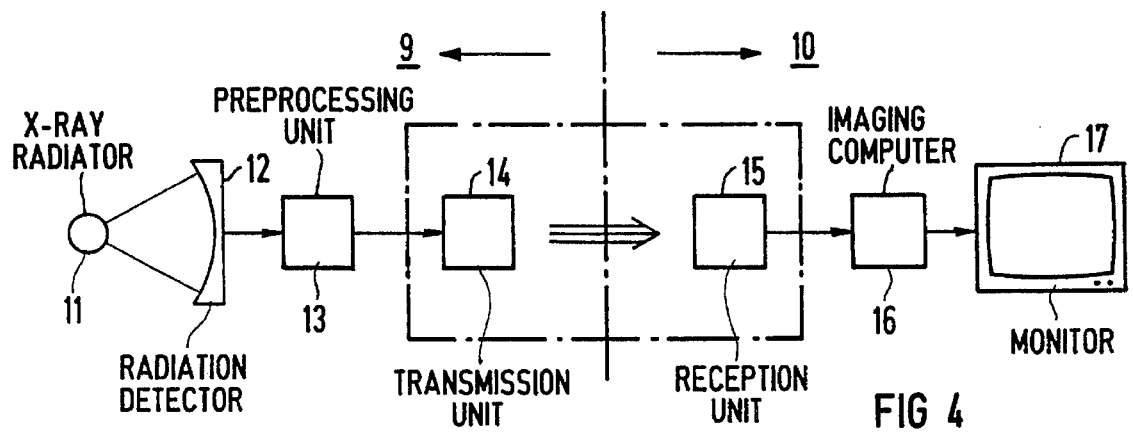
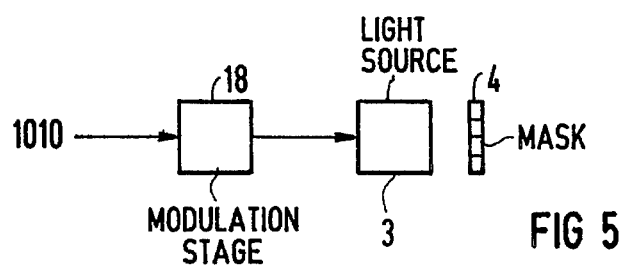
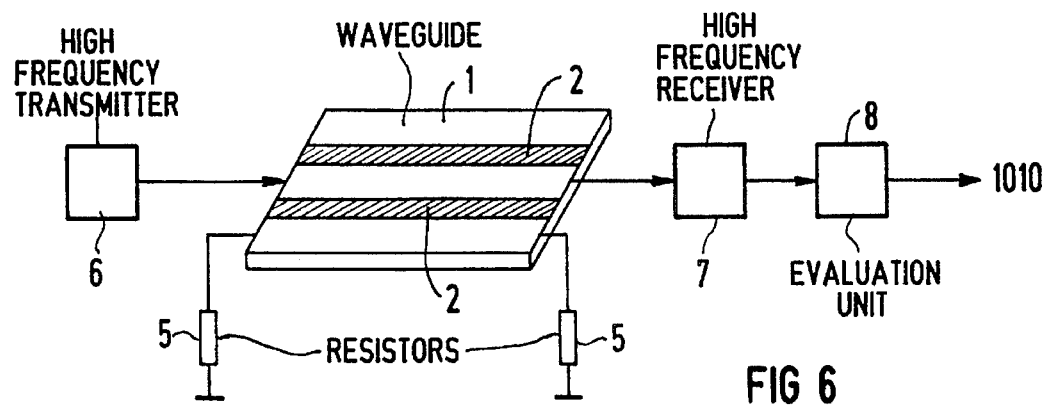

NON-CONTACTING OPTICAL DATA TRANSMISSION SYSTEM

BACKGROUND OF THE INVENTION

1. Field of the Invention

The present invention is directed to a non-contacting optical data transmission system for transmitting data between two components disposed at a distance from one another in a non-contacting fashion, such as for transmitting data between a stationary component and a movable component.

2. Description of the Prior Art

It is often necessary in various technological fields to transmit data in a non-contacting fashion between two components which are disposed a distance from each other. This requirement arises, for example, in the field of computer tomography, wherein a radiation transmitter and a radiation receiver are rotated on a stationary frame around an examination subject to obtain data from various projection angles. The output signals of the rotating radiation detector must be transmitted to components located on the stationary frame, or to other stationary components, for processing the data. A similar situation exists in the field of nuclear medicine.

In the computer tomography field, such data transmission has conventionally taken place by means of mechanical wiper rings, or by a direct optical transmission between a transmitter and a receiver.

SUMMARY OF THE INVENTION

It is an object of the present invention to provide a non-contacting optical data transmission system which allows data transmission between components which are moving relative to each other, and also allows data transmission between stationary components.

The above object is achieved in accordance with the principles of the present invention in a non-contacting optical data transmission system having a waveguide with one end coupled to an high-frequency generator and an opposite end coupled to an high-frequency receiver, with the basic material of the waveguide consisting of photosensitive material. An illumination pattern is generated on the waveguide by a light source and a mask. This illumination pattern modifies the reflection behavior of the waveguide such that the amplitude of the high-frequency signal transmitted through the waveguide is correspondingly modulated, by keying the light source according to the information to be transmitted.

In the data transmission system of the invention, data transmission ensues in non-contacting fashion with optically-produced amplitude modulation of a high-frequency wave. A continuous information flow is assured regardless of whether the transmitter and receiver are disposed stationary relative to each other, or movable relative to each other.

The invention can generally be employed for data transmission between a transmitter and receiver which are moved relative to each other, and/or for stationary transmitters and receivers, for non-contacting data transmission, wherein a separation of potential is assured. The data transmission system is particularly suitable for employment in computer tomography and nuclear medicine.

Light-induced DBR (distributed Bragg reflection) microwave filter structures form the basis of the invention. Such microwave filter structures are periodically "disturbed" waveguides or line sections, with the periodically distributed inhomogeneities generating partial signal reflections.

Frequency-selective waveguides or line structures can be employed using constructive interference. Heretofore, spatially or chronologically fixed DBR structures have been achieved by using waveguides having a spatially periodic variation in the layer thicknesses or the refractive index within the basic dielectric material.

When the non-conductive, basic dielectric material of the waveguide is partially or completely replaced by photosensitive semiconductor material, the previously uniform waveguide arrangement can be converted into a periodically disturbed (impermanent) DBR structure with a spatially periodic continuous light infeed.

DESCRIPTION OF THE DRAWINGS

FIG. 4 is a block diagram showing the employment of a data transmission system constructed in accordance with the principles of the present invention in a computer tomography apparatus.

FIG. 5 is a schematic illustration of the structure of a transmission unit for use in the data transmission system of the invention.

FIG. 6 is a schematic illustration of a reception unit for use in the data transmission system of the invention.

DESCRIPTION OF THE PREFERRED EMBODIMENTS

Figure 1:
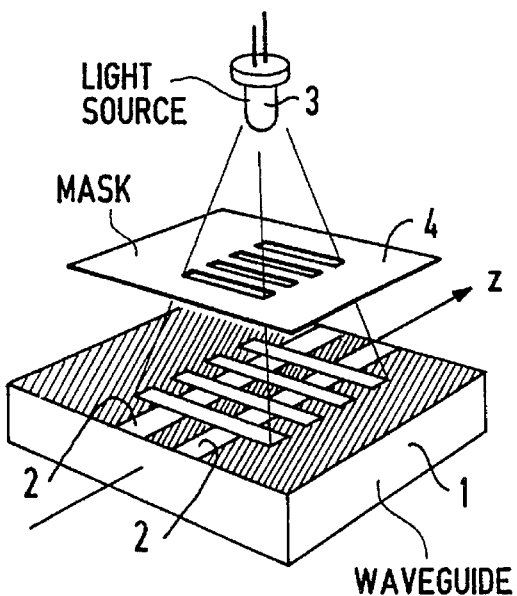
FIG. 1 illustrates the principles of a light-induced periodic conduction structure, as employed in accordance with the principles of the present invention in a non-contacting optical data transmission system.

FIG. 1 shows a waveguide 1 in the form of a silicon coplanar line, having a number of regions 2 of photosensitive material. An illumination pattern is generated on the regions 2 by means of a light source 3, for example a light-emitting diode, and a mask 4. A periodic change in the photoconductivity of the waveguide material arises due to the internal optoelectrical effect, i.e., the optical generation of electron-hole pairs in the semiconductor material. This results in the "inscribing" of a conductivity grating in the semiconductor material. Optically excited line sections are interconnected with darkened line sections to form a light-induced, periodic line structure.

For fashioning the grating according to the Bragg condition, it is necessary that $\Lambda = m\,(\lambda/2)$, wherein $m = 1, 2, \ldots$, $\Lambda$ is the period length of the grating, and $\lambda$ is the wavelength of the microwave signal on the waveguide 1.

Due to constructive interferences and photo-induced wave attenuation, selective overall reflection factors of up to approximately 50% are achieved, but these are not chronologically and spatially fixed. Due to the aforementioned generation of electron-whole hole pairs, the optical power required for control is low.

Figure 2:
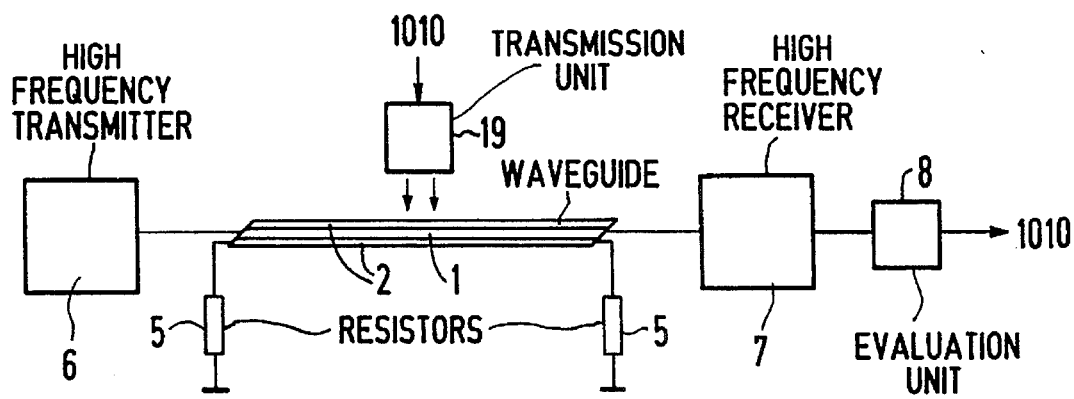
FIG. 2 is a block circuit diagram of a data transmission system constructed in accordance with the principles of the present invention.
Figure 3:
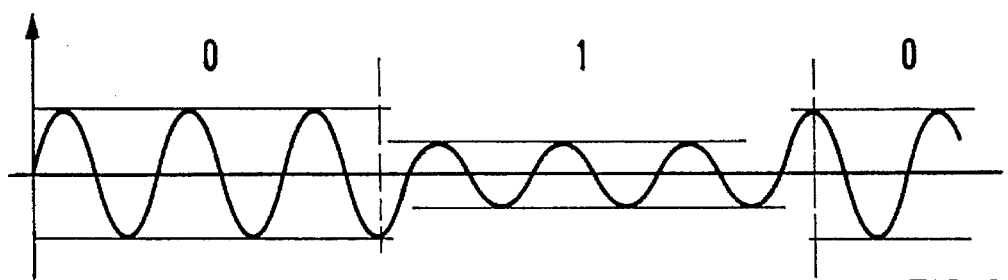
FIG. 3 shows the signal curve at the receiver for data transmitted according to the system shown in FIG. 2.

The above-described principle is inventively utilized for data transmission in the system shown in FIG. 2. The system shown in FIG. 2 includes the waveguide 1 and the transmission unit, formed by the light source 3 and the mask 4, which irradiates the waveguide 1. Resistors 5 produce a reflection-free line termination. A high-frequency generator 6 is connected to the input of the waveguide 1, and a high-frequency receiver 7 is connected to the output of the waveguide 1. The high-frequency receiver 7 feeds an evaluation unit 8. The light from the transmission unit 19 is binarily modulated, i.e., it is switched on and off (keyed) dependent on the data to be transmitted. The generation of light, for example, represents a binary one and the absence of light represents a binary zero. The high-frequency signal is supplied to the waveguide 1 with a constant amplitude and constant frequency at the beginning of the line, and is tapped reflection-free at the end of the line. The reflection behavior of the waveguide 1 is modified by the grating illumination according to FIG. 1. An increase in the reflection factor of up to 50% arises due to the activation of the light source 3. This means that, when the light source 3 is not energized, the amplitude of the received signal is unvaried in comparison to the infed signal. By contrast, an attenuation of the amplitude of the received signal compared to the input signal of up to 50% ensues when the light source 3 is energized, due to reflection at the location of the DBR structure generated by the illumination. FIG. 3 shows an exemplary reception signal. Sequences consisting of ones and zeros arise as shown in FIG. 3, which represent the signal to be transmitted, and which can be detected in the evaluation unit 8 on the basis of the amplitude-modulated signal received by the receiver 7.

FIG. 4 shows the rotating part 9 and the stationary part 10 of a computer tomography apparatus including an x-ray radiator 11, a radiation detector 12, a data pre-processing unit 13, a transmission unit 14, a reception unit 15 and an imaging computer 16, connected to a monitor 17 for reproduction of images. The x-ray radiator 11 rotates in a known manner around a patient together with the detector 12, so that the patient is penetrated by radiation from various directions. The imaging computer 16 calculates an image of the patient from the output signals of the detector 12. The data from the detector 12 are transmitted from the rotating part 9 to the stationary part 10 by means of a data transmission system as shown in FIG. 2. The transmission unit 14 corresponds to the transmission unit shown in FIG. 5, whereas the reception unit 15 corresponds to the arrangement shown in FIG. 6.

The basic structure of the transmission unit is shown in greater detail in FIG. 5. The transmission unit includes a modulation unit 18, which modulates the light of the light source 3 according to the signal to be transmitted. The modulated light is directed through the mask 4. The reception unit 15 shown in FIG. 6 includes a waveguide 1 which is fashioned in conformity with FIG. 1, and is employed in a structure in conformity with FIG. 2.

Figure 7:
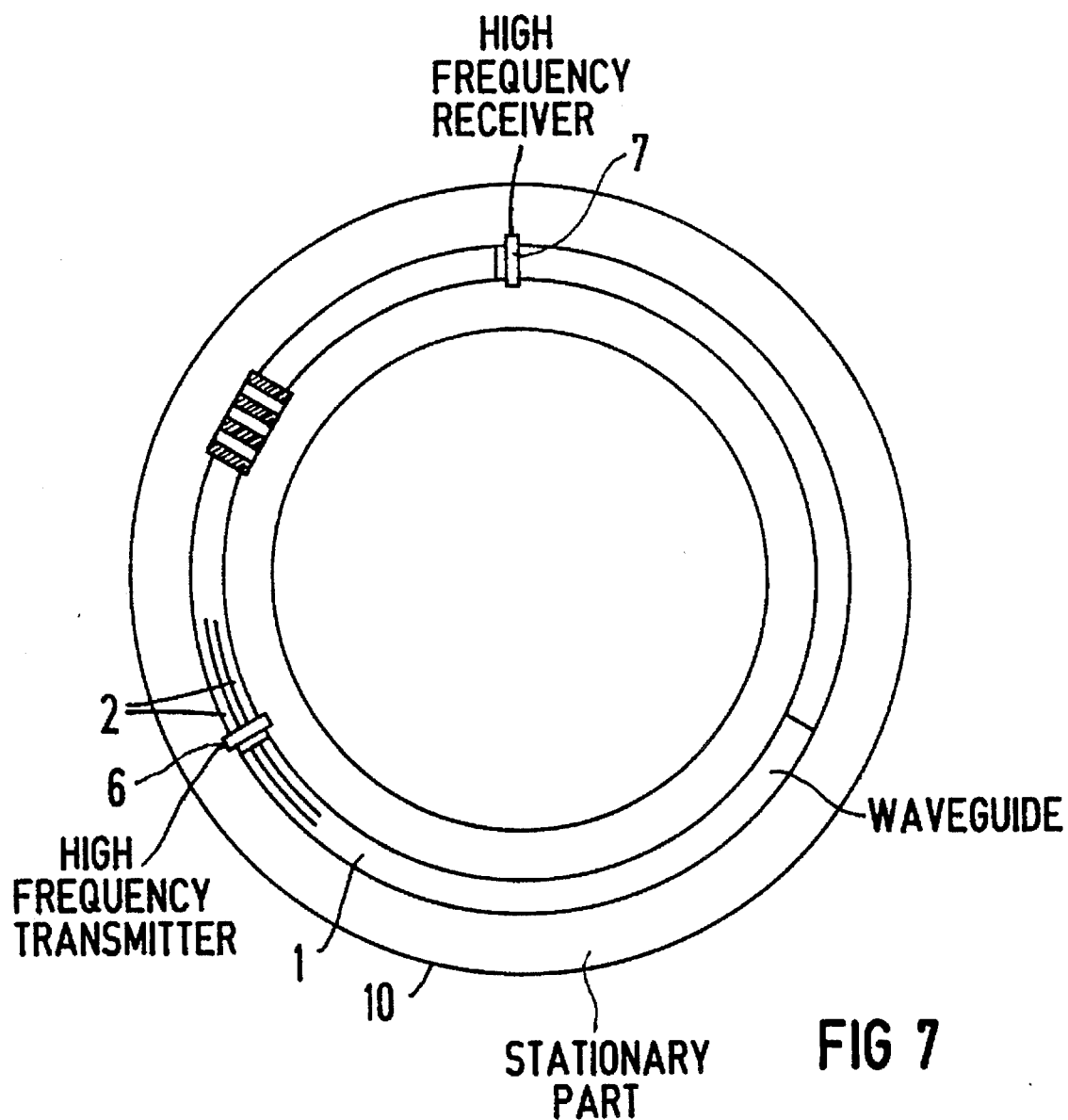
FIG. 7 shows a detailed embodiment of the arrangement of the components of the data transmission system of the invention arranged on a computer tomography apparatus.

FIG. 7 shows the arrangement of the relative components on the stationary part 10 of the computer tomography apparatus of FIG. 4. The stationary part 10 is in the form of a ring on which the waveguide 1, which is annularly fashioned, is located. The basic dielectric material of the waveguide 1 has been entirely or partially replaced by photosensitive material along the entire circumference (length) of the waveguide 1. The waveguide 1 may be divided, for example, into three sections, each section representing a complete reception unit according to FIG. 6. The transmission unit according to FIG. 5 is located on the rotating part (not shown in FIG. 7) which is disposed opposite the ring forming the stationary part 10. This transmission unit emits the data signal by activating and deactivating the light source 3 as explained above. The transmitted information exemplified by FIG. 3 can be detected at the receiver of the segment of the waveguide 1 which has been respectively illuminated. An illumination pattern generated by the transmission unit 14 is schematically indicated in FIG. 7.

Although modifications and changes may be suggested by those skilled in the art, it is the intention of the inventors to embody within the patent warranted hereon all changes and modifications as reasonably and properly come within the scope of their contribution to the art.

We claim as our invention:

1. A non-contacting optical data transmission system comprising:

a high-frequency waveguide having first and second ends, and consisting of photosensitive material;

a high-frequency transmitter coupled to said first end of said waveguide and a high-frequency receiver coupled to said second end of said waveguide;

means, including a light source and a mask, for generating an illumination pattern on said photosensitive material of said waveguide for modifying the reflection behavior of said waveguide in accordance with said illumination pattern for varying the amplitude of a signal transmitted through said waveguide from said high-frequency transmitter to said high-frequency receiver;

means for keying said light source dependent on data to be transmitted; and means for analyzing the amplitude of said signal received by said high-frequency receiver for recovering the transmitted data.

2. A data transmission system as claimed in claim 1 wherein said light source and said waveguide are movable relative to each other.

3. A data transmission system as claimed in claim 2 wherein said light source is disposed on a first part of a computer tomography apparatus and wherein said waveguide is disposed on a second part of said computer tomography apparatus, said first and second parts being rotatable relative to each other.

4. A non-contacting optical data transmission system as claimed in claim 1 wherein said means for generating an illumination pattern comprises means for generating an impermanent illumination pattern on said photosensitive material of said waveguide for temporarily modifying the reflection behavior of said waveguide in accordance with said illumination pattern for varying the amplitude of a signal transmitted through said waveguide from said high-frequency transmitter to said high-frequency receiver.

\* \* \* \* \*